(12) United States Patent
Mirshahi et al.

(10) Patent No.: US 7,968,302 B2
(45) Date of Patent: Jun. 28, 2011

(54) DETECTION OF VENOUS THROMBOEMBOLIC DISEASES BY MEASUREMENT OF D-DIMERS AND SOLUBLE FIBRIN LEVELS

(75) Inventors: Bibi Shah Soltan Mirshahi, Villejuif (FR); Jeannette Soria, Taverny (FR)

(73) Assignees: Diagnostica Stago, Asnieres (FR); Assistance Publique - Hopitaux de Paris, Paris (FR)

( * ) Notice: Subject to any disclaimer, the term of this patent is extended or adjusted under 35 U.S.C. 154(b) by 157 days.

(21) Appl. No.: 12/299,169

(22) PCT Filed: May 3, 2007

(86) PCT No.: PCT/FR2007/000764
§ 371 (c)(1),
(2), (4) Date: Dec. 22, 2008

(87) PCT Pub. No.: WO2007/128916
PCT Pub. Date: Nov. 15, 2007

(65) Prior Publication Data
US 2009/0305301 A1 Dec. 10, 2009

(30) Foreign Application Priority Data
May 5, 2006 (FR) .................................. 06 04072

(51) Int. Cl.
*G01N 33/53* (2006.01)
(52) U.S. Cl. ........................... 435/7.1; 435/7.2; 436/518
(58) Field of Classification Search .................. None
See application file for complete search history.

(56) References Cited

U.S. PATENT DOCUMENTS
5,114,845 A  5/1992 Randby
5,206,140 A * 4/1993 Marder et al. ............... 435/7.1

FOREIGN PATENT DOCUMENTS
EP 0347933 12/1989
WO 02/18628 3/2002

OTHER PUBLICATIONS

Scott K. Brimble et al., "Evaluation of the Combination of a Bedside D-Dimer Assay and Enzyme-Linked Immunosorbent Soluble Fibrin Assay in Patients with Suspected Venous Thromboembolism", Thrombosis Research, Nov. 1, 1997, pp. 291-297, vol. 88, No. 3, Elsevier Science Ltd., USA.
Satoshi Ota et al., "Diagnosis of Deep Vein Thrombosis by Plasma-Soluble Fibrin or D-Dimer", American Journal of Hematology, Aug. 2005, pp. 274-280, vol. 79, No. 4, Wiley-Liss, Inc.
Y.S. Arkel et al., "The use of coagulation activation markers (soluble fibrin polymer, TpPTM, prothrombin fragment 1.2, thrombin-antithrombin, and D-dimer) in the assessment of hypercoagulability in patients with inherited and acquired prothrombotic disorders", Blood Coagulation and Fibrinolysis, Apr. 2002, pp. 199-205, vol. 13, No. 3, Lippincott Williams & Wilkins.
French Preliminary Search Report and Written Opinion, mailed Dec. 12, 2006 in corresponding French Patent Application No. FR 0604072.
International Search Report dated Sep. 28, 2007, in PCT application.

* cited by examiner

*Primary Examiner* — Jacob Cheu
(74) *Attorney, Agent, or Firm* — Young & Thompson (57) ABSTRACT

A method and a test for detecting coagulation activation, in particular when it is responsible for thromboembolic venous diseases; employs assaying D-dimers and assaying the soluble fibrin produced during a fibrinolysis process activated in a blood sample. The method of the invention pertains to comparing the level of D-dimers corresponding to degradation of soluble fibrin and the level of D-dimers of the sample with normal threshold values. The test of the invention may also be used to determine whether anti-coagulation is sufficient in a patient.

20 Claims, 2 Drawing Sheets

DETECTION OF VENOUS THROMBOEMBOLIC DISEASES BY MEASUREMENT OF D-DIMERS AND SOLUBLE FIBRIN LEVELS

The present application relates to a method and a test for detecting the activation of coagulation, in particular when it is linked to thromboembolic venous diseases, using an assay of D-dimers and assaying the soluble fibrin during a coagulation activation process in blood.

BACKGROUND OF THE INVENTION

Fibrinolysis is the process of degradation of fibrin in the blood. Fibrinolysis is involved in a number of physiopathological processes and is triggered in situations when tissue plasminogen activator and plasminogen bind to fibrin, forming a ternary fibrin-plasminogen complex within which the t-PA has a high affinity for plasminogen, entraining the generation of plasmin, an enzyme which degrades fibrin into D-dimers. In the absence of fibrin, t-PA has little affinity for plasminogen, explaining the fact that circulating fibrin is not degraded.

Degradation of fibrin, or fibrinolysis, leads to the formation of degradation products especially comprising "D-dimer" fragments. Said D-dimers are associated with the E fragment from degradation of another fibrin monomer molecule forming the DDE complex, but even in that form, they are routinely termed D-dimers.

The fibrin undergoing the fibrinolysis process is formed by conversion of fibrinogen under the action of a coagulation enzyme, namely thrombin. During coagulation activation, the thrombin generated thus induces the formation of deposits of fibrin which will constitute the thrombus and the formation of soluble fibrin. To accomplish this, thrombin attacks four peptide bonds of the fibrinogen located respectively on the 2 A alpha and the 2 B beta chains, causing the liberation of two A fibrinopeptides from the two A alpha chains and the liberation of two B fibrinopeptides from the B beta chains, resulting in the formation of fibrin monomers which polymerize spontaneously into the form of a polymer by dint of hydrogen bonds established by interaction between A and B polymerization sites unmasked during liberation of the A and B fibrinopeptides and the a and b sites which are available at the ends of the gamma and beta chains respectively. The fibrin polymer is then immediately stabilized by factor XIII(a). Thrombin generation is much greater during in vitro tests than that which takes place in vivo. For this reason, the generation of fibrin monomers is much slower in the in vivo coagulation activation process than in that generated in vitro, which causes part of the monomers formed to polymerize to produce insoluble fibrin constituting the thrombus and another part of said monomers to react with fibrinogen in which the a and b sites are accessible, or with fibrinogen degradation products to produce soluble fibrin in which fibrin monomers are associated with fibrinogen.

Determining the concentration of soluble fibrin is important in order to witness the activation of coagulation in a patient. Said determination may be carried out using samples of blood or plasma obtained from a blood sample taken from a patient.

It has been shown that assaying soluble fibrin is a useful complement to assaying fibrinolysis degradation products, since soluble fibrin can detect coagulation activation which is under way while the concentration of D-dimers indicates degradation of a thrombus, even if the activation coagulation process is stopped.

In summary, the D-dimer plasma level is increased while the fibrin clot degrades in vivo. Hence, if the thrombus is present and undergoing degradation, the level of D-dimers is high, whether coagulation persists or is stopped. In contrast, the level of soluble fibrin is raised only if coagulation persists.

Compared with the level of D-dimers, specific measurement of the soluble fibrin plasma level thus allows a determination of the coagulation occurring in a patient at the moment the sample to be analyzed is taken, along with an evaluation of the coagulolytic balance.

Determining the level of D-dimers in the sample, termed the base level, is thus a reflection of the degradation of the thrombus which occurs in vivo, while determining the level of D-dimers obtained after exogenic addition of a specific fibrin thrombolytic agent represents the sum of the base D-dimers and the D-dimers deriving from degradation of soluble fibrin, also termed circulating fibrin.

International patent application WO-A-02/18628 describes a method for assaying soluble fibrin in a blood sample, necessitating bringing plasma into contact with a plasminogen activator with a high affinity for soluble fibrin (PA-Fb sp), followed by determining the level of fibrin degradation products (D-dimers). The difference between the concentration of D-dimers in a sample treated with PA-Fb sp and that of the base D-dimers determined on plasma not treated with PA-Fb sp thus represents the D-dimers linked to soluble fibrin degradation. The inventors have now observed that the method proposed in prior art International application WO-A-02/18628 may advantageously be supplemented to be carried out in the context of the diagnosis of thromboembolic venous diseases, as well as the diagnosis and monitoring of disseminated intra-vascular coagulations (DIVC). It also allows a determination of whether anti-coagulant treatment will be effective to be made.

Thromboembolic venous diseases principally comprise venous thromboses of the limbs and pulmonary embolism, the latter resulting from a complication of the first thromboses. Venous thromboses other than those of the limbs are also encountered, since all venous territories can undergo a thrombosis. The renal veins and mesenteric veins can be cited in particular among those which are at the origin of pathologies. Thromboembolic diseases such as deep venous thrombosis (DVT) and/or pulmonary embolism (PE) are life-threatening diseases and represent a large proportion of the disabilities and deaths in industrialized countries, and establishing a diagnosis of these diseases is vital in completing investigations by imaging examinations such as ultrasound imaging for the diagnosis of venous thromboses and scintography or angiography to diagnose pulmonary embolisms. These exploratory methods are tricky to carry out and cannot always be carried out rapidly enough.

As a result, there is a continuing need for defining a test allowing rapid diagnosis of thromboembolic disease in a patient, that diagnosis including the possibility of excluding that disease without necessarily having recourse to additional investigations.

BRIEF SUMMARY OF THE INVENTION

In the field of the diagnosis of diseases linked to coagulation, the capacity of using D-dimers if their levels are normal is known to be a negative indicator of thrombosis since the principle that the formation of a thrombus involves both activation of coagulation and fibrinolysis is acknowledged.

However, the only D-dimers count measured until now lacks specificity and cannot allow one to conclude with certainty that an intra-vascular thrombus has formed, as the D-dimers present in the circulation may derive from the degradation of extra vascular fibrin deposits. The D-dimers formed in situ may then pass into the circulation, hence producing a high level of circulating D-dimers. In the context of the present invention, the inventors have evaluated the pertinence of a diagnosis based on the D-dimers test in association with a rapid test for determining soluble fibrin which is representative of intra-vascular coagulation activation. This combination of assays has proved to be of advantage in the context of a diagnosis of deep venous thrombosis (DVT) and/or pulmonary embolism (PE) as well as in the context of a diagnosis of disseminated intra-vascular coagulation (DIVC). The soluble fibrin test carried out, termed SDF for soluble degradable fibrin, allows the soluble fibrin to be assayed by determining the degradation products generated during its degradation by tissue plasminogen activator (or another thrombolytic agent such as a specific plasminogen activator of fibrin) supplied exogenically to a sample.

Thus, the invention concerns an in vitro method for diagnosing coagulation activation starting from a blood sample removed from a patient, comprising:
  i) measuring the quantity of fibrin degradation products contained in the test sample, consisting of measuring the quantity of D-dimers present in the sample and constituting the base Level of D-dimers;
  ii) treating the sample by incubation with a plasminogen activator with a high affinity for fibrin (Pa-Fb sp) under conditions allowing degradation of the soluble fibrin contained in the sample into degradation products without resulting in the degradation of fibrinogen, and measuring the quantity of D-dimers contained in the treated sample;
  iii) calculating the difference between the quantity of D-dimers measured after activation by the Pa-Fb sp activator in step ii) and the quantity of D-dimers before said activation measured in step i), said difference constituting the degree of degradation of the soluble fibrin (SDF);
  iv) comparing the level of D-dimers measured in step i) with a normal threshold value determined for said degradation product and comparing the level of SDF calculated in step iii) with a normal threshold value determined for SDF.

DETAILED DESCRIPTION OF THE INVENTION

When the assay method is carried out, starting from a sample, it is possible to determine the risk of thromboembolic disease: this risk exists if at least one of the calculated levels of said fibrin degradation product or SDF (D-dimers) is higher than the normal value and that risk is excluded when the calculated level of said degradation product of fibrin and the level of SDF are lower than the respective normal threshold values.

The diagnostic method of the invention is applicable to the diagnosis of blood coagulation whether the process of coagulation is localized (such as deep venous thromboses) or generalized (such as in the case of DIVC).

If appropriate, before adding the plasminogen activator in step a)ii) above, a mixture of citric acid and sodium citrate is added to the portion of the sample on which the soluble fibrin degradation products are determined.

The reagent used to assay the degradation products is selected to measure a given group of degradation products. As an example, antibodies with a predetermined specificity towards a particular type of fibrin degradation products are used.

When the concentration of base D-dimers measured in step i) has a value of more than the threshold value of 500 ng/ml [nanograms/milliliter], the Level of D-dimers is considered to be increased. When the concentration of D-dimers corresponding to soluble fibrin degradation and which is calculated in step iii) has a value of more than the threshold value of 300 ng/ml determined in healthy subjects, it is considered to be increased.

Said threshold values have been determined with a reagent constituted by an antibody from the "Lia-test" test from Diagnostica Stago or from the VIDAS test from Bio-Mérieux. For the other reagents, the threshold value should be determined by comparison with the results obtained with said reagents.

When the D-dimer measurements and the soluble degradable fibrin measurements have been carried out, it is assumed that in the patient whose blood sample is being tested, a risk of thromboembolic disease exists when the level of (D-dimers) produced by degradation of the base fibrin is 500 ng/ml or more or when the level of soluble fibrin determined by the difference between the level of D-dimers present in the plasma treated with the specific fibrin plasminogen activator and that of the base Level of D-dimers is more than the threshold value, for example 300 ng/ml.

The biological sample is preferably a biological liquid, for example a plasma or blood sample, or a puncture liquid, provided that the level of plasminogen in that liquid is identical to that of plasma. In the case of puncture liquids containing little plasminogen, adding Glu-plasminogen must be considered so that the plasminogen concentration is close to that of plasma.

The plasminogen activator with a high affinity for fibrin (i.e. which only activates the plasminogen in the fibrin) used in the method for assaying soluble fibrin by generating specific degradation products may be selected from many compounds known to be plasminogen activators. However, certain of them degrade both fibrinogen and fibrin, such as streptokinase and urokinase. These compounds are not suitable for use in the method of the invention as they result in the degradation of fibrin giving rise to fibrinogen degradation products which interfere with those resulting from fibrin degradation.

Another group of plasminogen activators is constituted by compounds described as having a high specificity for degrading fibrin, compared with fibrinogen. The method of the invention advantageously uses the specificity of this other group of compounds to carry it out and, for example, uses:
  tissue plasminogen activator (t-PA) or its derivatives such as TNK-tPA which is a t-PA mutant which has a very high specificity for fibrin (Cannon C P et al, "TNK tissue plasminogen activator compared with front loaded altephase in acute myocardial infarction results of the TIMI 10B trial", Thrombolysis in Myocardial Infarction (TIMI) 10B Investigators, Circulation 98 (25), 2805-14, 1998);
  the activator deriving from *Desmodus rotundus* (bat-tpa or vPA=vampire bat salivary plasminogen activator) or its derivatives: DSPAs=*Desmondus rotundus* salivary PAs, FEKP=DSPA alpha 1 and alpha 2, EKP=DSPA beta, KP=DSPA gamma (Bringmann et al: "Structural features mediating fibrin selectivity of vampire bat plasminogen activators", J Biol Chem 270, 25596-603, 1995), staphylokinase (SAK), a polypeptide secreted by Staphylococcus aureus (Collen D: "Staphylokinase: a potent, uniquely fibrin-selective thrombolytic agent", Nat Med, 4-279-84, 1998; Sakharov D V et al: "Fibrin specificity of a plasminogen activator affects the efficiency of fibrinolysis and responsiveness to ultrasound: comparison of nine plasminogen activators in vitro".

Thromb Haemos, 81, 605-12, 1999) or one of its mutants (Collen D et al, "Recombinant staphylokinase variants with altered immunoreactivity. I: Construction and characterization". Circulation 94, 197-206, 1996).

To carry out the diagnostic method described above, anti D-dimer antibodies are used to carry out the two assays (base D-dimers and D-dimers after action of specific fibrin plasminogen activator) of the method of the invention. Said antibodies have been described in the prior art and are also commercially available, for example from Diagnostica Stago under the name "Lia-test" or under the name "Vidas" from Bio-Mérieux.

In order to be compared, the assays of steps i) and ii) must use the same anti D-dimer antibody.

The D-dimers resulting from the degradation of soluble fibrin in the presence of Pa-Fb sp may be assayed using any routine analyte assay technique such as ELISA type methods, sensitive latex bead agglutination methods (of the type used in the Lia-test), immunochromatographic methods, etc. Examples of the various commercially available D-dimer assay tests which may be cited are ASSERACHROM D-Di or STA LIATEST D-Di, both sold by Diagnostic Stago. However, in the context of the present invention, the conditions for use of the ELISA test from ASSERACHROM D-Di have advantageously been modified to shorten the test (15 min incubation with immobilized antibody and 15 minutes with antibody labeled with peroxidase).

Advantageously, the in vitro diagnostic method of the invention also comprises treatment of a positive control sample, in particular a positive control plasma.

To obtain the positive control plasma, the plasma is first incubated with a small quantity of thrombin for a predetermined period to allow the formation of soluble fibrin, without forming a clot of fibrin. The coagulation process which has been triggered is then blocked by adding a thrombin inhibitor to prevent the reaction from continuing. Hirudin or heparin, for example, may be used as the inhibitor.

The plasma incubation time and the concentrations of thrombin and inhibitor for blocking are advantageously determined so as to achieve coagulation activation resulting in the generation of soluble fibrin without forming a fibrin clot.

Incubation in the presence of coagulation activator (thrombin) is preferably carried out for an incubation period of 2 minutes at ambient temperature. The inhibitor is then added in large excess to be certain of blocking coagulation.

if it is hirudin, this is advantageously used in a final concentration of 100 µg/ml for a final concentration of thrombin of 0.18 U/ml;

if it is heparin, this is used in a final concentration of 500 U/ml when the final concentration of thrombin used is 0.18 U/ml.

In another advantageous implementation of the invention, the in vitro diagnostic method also comprises treatment of a negative control sample, in particular a negative control plasma. A description concerning the preparation of said controls is given in the examples along with supplemental details.

Evaluation of soluble fibrin in accordance with the present invention employs a first step for degradation of soluble fibrin by Pa-Fb sp, followed by measuring the specific degradation products resulting from the action of Pa-Fb sp.

It is vital for the results of the method of the invention to be obtained as rapidly as possible, while being representative of the quantity of soluble fibrin present in the sample. To this end, the conditions for using the Pa-Fb sp must be determined so that degradation of the soluble fibrin is rapid and it is not accompanied by "contaminating" degradation of circulating plasmatic fibrinogen giving rise to degradation products interfering with those from soluble fibrin in the assay.

The doses of Pa-Fb sp to be used and the incubation period with the plasma are thus selected to induce an increase in the level of fibrin degradation products which is highest in the positive controls, and a practically zero increase in the negative controls (i.e. those which have not undergone treatment with a coagulation activator).

Various fibrinolysis activators allowing specific degradation of soluble fibrin may be used in the context of the present invention. Advantageously, the Pa-Fb sp is selected from a group constituted by the activators cited above, namely: t-PA or its derivatives, VPA or its derivatives and staphylokinase or one of its mutants. Preferably, t-PA or staphylokinase is used, more preferably t-PA.

Under the conditions wherein the samples are incubated for 15 minutes at 37° C., the final concentration of tested staphylokinase is in the range 1 to 12 µg/ml. The final retained concentration is advantageously 10 µg/ml. The incubation period may be modified and its variation is determined as a function of the nature and the concentration of the Pa-Fb sp used.

The t-PA is advantageously used in a final concentration range in the range 1 to 2.5 µg/ml. Preferably, the t-PA is used in a concentration of 2 µg/ml for an incubation period of 15 minutes at 37° C.

In a particular implementation of the invention, degradation of soluble fibrin by the plasminogen activator without degradation of fibrinogen may be blocked after degradation of the soluble fibrin by adding a plasmin inhibitor, for example aprotinin. Particular characteristics for using aprotinin or another plasmin inhibitor in equivalent manner are given in the examples. The quantity of aprotinin used is, for example, equivalent to the quantity of plasminogen activator used. Thus, the plasmin inhibitor is added after 15 minutes incubation at 37° C. with the plasminogen activator.

In a particular implementation of the invention, prior to adding the plasminogen activator, an anticoagulant such as a solution containing citric acid and sodium citrate may be added both to the assayed sample and to the control samples. The quantities and mode of adding the citric acid and sodium citrate are indicated in the examples.

In the context of the present invention, the diagnostic method described above is applied to investigating the formation of a venous thrombus.

In a particular application of the diagnostic method of the invention, the method is carried out for diagnostic exclusion of a deep venous thrombosis.

In a particular implementation of the invention, the diagnostic method is carried out for diagnostic exclusion of a pulmonary embolism.

In a particular implementation of the invention, the method is carried out on a blood sample taken from a patient prior to carrying out an anticoagulant treatment.

In principle, assaying soluble fibrin for the diagnostic exclusion of a venous thrombosis must be carried out before any anticoagulant treatment. If the patient undergoes treatment with anti-coagulants, the concentration of soluble fibrin reduces very quickly and reaches normal values. In treated patients, determination of the concentration of soluble fibrin in the plasma can only determine whether the anti-coagulant was effective.

In a particular implementation of the method, the soluble fibrin assay is carried out using t-PA as the plasminogen activator.

Other characteristics of the invention will become apparent from the following examples and figures.

EXAMPLES

Example N° 1

Figure 1:
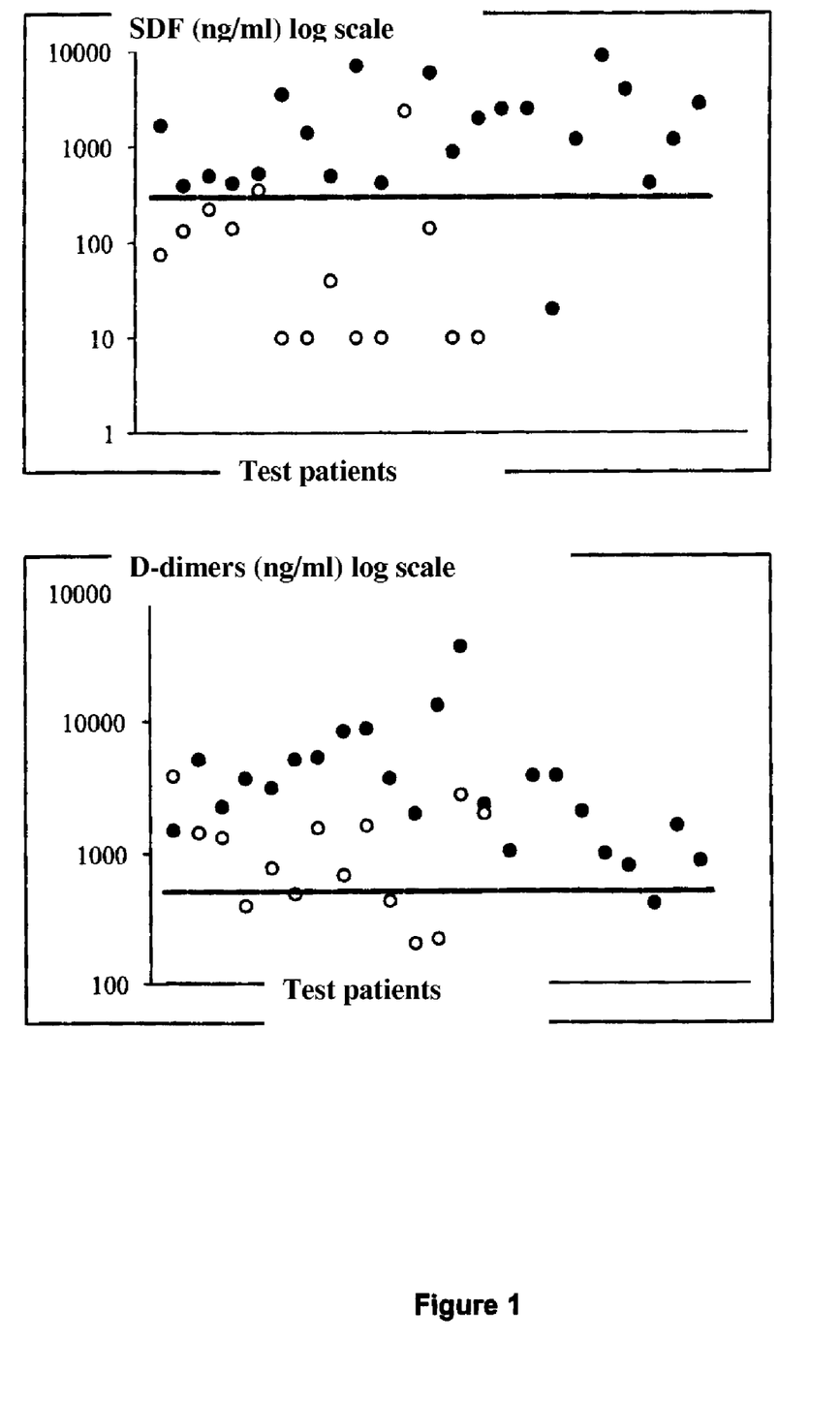
FIGS. 1 and 2 respectively show a comparison of D-dimers and SDF in patients with suspected pulmonary embolism or with suspected deep venous thrombosis. In each case, the black circles correspond to sick patients and the white circles to normal patients. The line shows the upper limit of the normal value.
Figure 2:
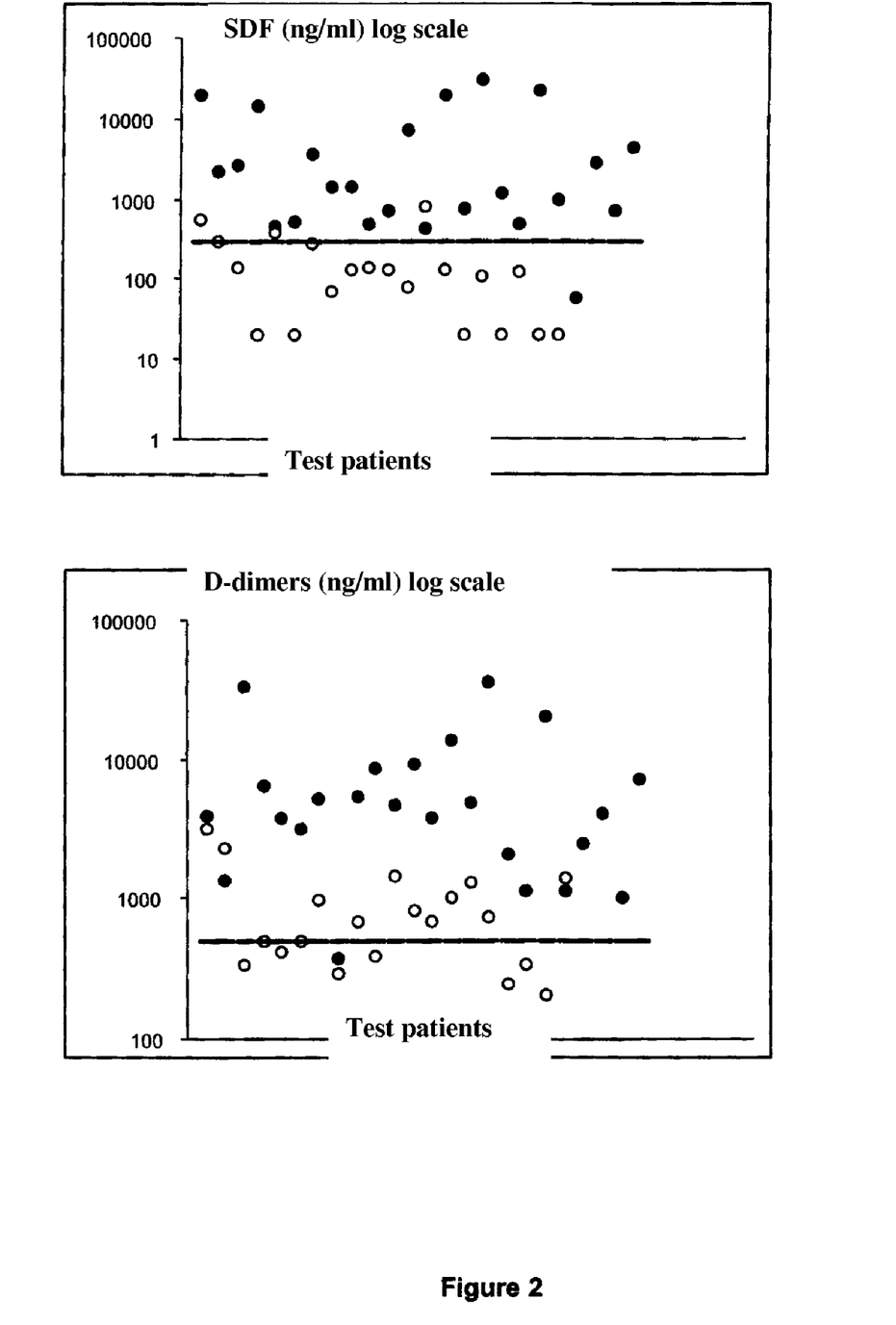

Selecting Concentration of Thrombin Used to Obtain a Positive Plasma Control Comprising Soluble Fibrin The positive control plasma was prepared using the following protocol:

| | |
|---|---|
| Normal plasma | 200 µl |
| Human thrombin (Stago, ref 00896), 0.5 to 1 U/ml (depending on plasma used) | 20 µl |
| Incubation 2 min at laboratory temperature. | |
| Hirudin (Knoll) 100 µg/ml (final concentration) or Heparin (Choay) 5000 IU/ml (final concentration) | 20 µl |

To verify:

that there is no clot formation in the tube;

that a commercial soluble fibrin detection test is positive (for example FS test from Stago Laboratories).

| | Positive control | Negative control |
|---|---|---|
| Plasma | 200 µl | 200 µl |
| Thrombin 1 U/ml or 0.5 U/ml | 20 µl | — |
| Physiological serum | — | 20 µl |
| 2 min (±10 sec) at ambient temperature | | |
| Heparin, 5000 IU/ml | 20 µl | — |
| Physiological serum | — | 20 µl |

Example N° 2

Determination of Quantity of Pa-Fb sp to be Used Under Defined Incubation Conditions To carry out the method of the invention, the quantity of activator to be added to the test sample must be such that it induces the generation of a lot of D-dimers in the positive control plasma as obtained in example n° 1, with a non significant generation of D-dimers in a negative control plasma (control not treated with thrombin).

Incubation of control plasmas and positive control plasmas (n=21) was thus carried out with different doses of Pa-Fb sp for 15 minutes at 37° C. At the end of the incubation period, the D-dimers were determined by Lia-test or by rapid ELISA (D-Di Stago) (incubation 15 minutes at 37° C. with capture antibody and 15 minutes at 37° C. with revealing antibody).

The results shown in Table II were obtained with the ELISA test.

Substantially analogous results were obtained with the Lia-test (n=5).

TABLE II

Degradation of soluble fibrin by increasing quantities of t-PA and SAK.

| | D-dimers (ng/ml) | Soluble fibrin* (ng/ml) | D-dimers (ng/ml) | Soluble fibrin* (ng/ml) |
|---|---|---|---|---|
| | Negative control | | Positive control | |
| No Pa-Fb sp addition | 375 | | 375 | |
| After staphylokinase | | | | |
| 10 | 400 | <50 | 1750 | 1375 |
| 2 | 390 | <50 | 1615 | 1240 |
| 1.5 | 375 | <50 | 1700 | 1325 |
| 1 | 350 | <50 | 1657 | 1282 |
| 0.5 | 410 | <50 | 1125 | 750 |
| After t-PA (µg/ml) | | | | |
| 2 | 350 | <50 | 1790 | 1415 |
| 1 | 360 | <50 | 1420 | 1045 |
| 0.5 | 360 | <50 | 1210 | 835 |

*soluble fibrin = Level of D-dimers after addition of t-PA or staphylokinase - base D-dimers before adding t-PA or staphylokinase.

The selected dose of Pa-Fb sp is that which produces:

an increase of <300 µg/ml in untreated control plasmas (negative controls);

the greatest increase in positive control plasmas.

From these results, it transpires that the preferred final concentrations of Pa-Fb sp to be used are:

2 µg/ml for t-PA: under these conditions, the dose of t-PA which can be neutralized by plasminogen activator inhibitors (POI) is negligible;

10 µg/ml for SAK lower doses of SAK induced a poor degradability of soluble fibrin in certain patients or certain positive controls, most probably due to the presence of anti-staphylokinase in the sample, which anti-staphylokinase may appear following infection by staphylococci).

Example N° 3

Assay of D-Dimers and Soluble Fibrin

In the investigation, the D-dimers and soluble fibrin were assayed in 87 consecutive patients consulted in Emergency units with suspected venous thrombosis and/or pulmonary embolism and who had received no treatment. In these patients, an ultrasound investigation was carried out to diagnose deep venous thromboses; a scintography or a pulmonary angiograph was carried out to diagnose pulmonary embolism. The D-dimers and soluble degradable fibrin (SDF) levels were determined before starting anti-coagulant treatment. It was shown that the sensitivity of the assay of soluble degradable fibrin was similar to that of the D-dimers assay (96% for D-dimers and for soluble degradable fibrin). Interestingly, the "false negatives" for the D-dimers and soluble degradable fibrin levels were observed in different patients. Thus, combining the two tests could increase the sensitivity of the diagnosis of thrombosis (100%). Further, the specificity of soluble degradable fibrin in diagnosing thromboembolic venous disease is greater (86% and 87% respectively for pulmonary embolism and for deep venous thrombosis) than that of D-dimers (36% and 42% respectively for pulmonary embolism and for deep venous thrombosis).

Rapid normalization of soluble degradable fibrin was observed in patients under anti-coagulant treatment at a curative dose. Once anti-coagulant treatment was instituted, the soluble fibrin level dropped. As a result, the soluble degradable fibrin can not be used as a diagnostic test in patients already treated with anti-coagulants. However, the soluble degradable fibrin may be useful for monitoring the anti-coagulant treatment. In conclusion, it is indicated that the level of soluble degradable fibrin in association with that of D-dimers is a useful clinical tool to predict or rule out pulmonary embolism and/or deep venous thrombosis.

Soluble fibrin is present during coagulation activation. Its increase is observed from the early stages of said activation.

In the prior art, several tests have already been developed to evaluate soluble fibrin in patients presenting a thrombosis but, because of the variability in the results of the available tests, the importance of determining soluble fibrin in a diagnosis excluding thromboembolic venous disease had not been established (1-21).

The aim of the present study is to evaluate the potential use of a novel test based on determining the level of soluble degradable fibrin which is simple, rapid and sensitive and highly specific for plasmatic soluble fibrin polymers.

This test is based on evaluating the D-dimers generated after incubating plasma with t-PA under conditions inducing degradation of soluble fibrin but not inducing the degradation of plasmatic fibrinogen. Thus, this test has been termed the soluble degradable fibrin test (SDF). In fact, despite the small number of fibrin monomers in the soluble fibrin, the fibrin monomers are cross-linked together because factor XIII activation coincides with the release of fibrinopeptide A, and in addition, activation of factor XIII by thrombin is accelerated by the presence of fibrin (22). Soluble degradable fibrin was selected from markers for the generation of thrombin in vivo, such as fibrinopeptide A (FPA, half life 3 minutes (23) or the thrombin anti thrombin complex (TAT, half life 15 minutes (24)), because its measurement may be more sensitive as it is less sensitive to measurement anomalies.

The present study was carried out to evaluate the performance of the diagnostic test based on a combination of the D-dimers and soluble degradable fibrin levels in untreated consecutive patients clinically suspected of pulmonary embolism (n=38) or deep venous thrombosis (n=49) taken into the Emergency units of 3 different centers. In the case of suspected deep venous thrombosis, the diagnosis was confirmed by examining ultrasound compression; a diagnostic of pulmonary embolism was confirmed either by scintography or by pulmonary angiography. The threshold value for the soluble degradable fibrin for a test which was considered to be positive was 300 ng/ml.

In this study, with the aim of analyzing the effects of anti-coagulation, profiles of the change of soluble degradable fibrin and D-dimers were also examined in patients suffering from pulmonary embolism and/or deep venous thrombosis, after starting the anti-coagulant treatment, to test the effectiveness of the therapy in thromboembolic disease.

Method and Apparatus

Plasma samples: blood was collected on 0.13 M citrate (1 part of citrate for 9 parts blood). After centrifuging at 2500 g for 15 minutes, plasma was collected and frozen at −20° C. until use.

However, when the soluble degradable fibrin level was very high, as is the case with intra-vascular coagulation (DIVC), the soluble degradable fibrin may form an insoluble complex during the freezing and defrosting steps and as a result, it is recommended that this test be carried out with freshly collected plasma.

The blood was obtained from healthy volunteers or from outpatients who had presented to Emergency units. The patients who had received an anti-coagulant treatment were considered for monitoring only. The population of patients consisted of consecutive patients presenting clinical signs of pulmonary embolism or deep venous thrombosis who had been diagnosed by ultrasound analysis of the compression of the proximal leg veins, by pulmonary scintography and by pulmonary angiography to verify the diagnosis.

Biological Tests

Determination of D-Dimers

The D-dimers were measured by agglutination of microparticles of latex coated with monoclonal antibodies against D-dimers using the Lia-test (Diagnostica Stago) in an STA apparatus or by ELISA using VIDAS (bio-Mérieux).

Measurement of Soluble Degradable Fibrin: Carried Out in 3 Steps

1—fibrin degradation: 20 µl of t-PA, 20 µg/ml (treated plasma) or 20 µl of physiological serum (untreated plasma) was added to 200 µl of plasma. After incubation for 15 minutes at 37° C., the plasmin generated was blocked by adding 20 µl of aprotinin (Pentapharm), 12.5 TIU/ml.

2—The D-dimers concentration was then determined using the Lia-test D-dimers test from Diagnostica Stago.

3—The soluble degradable fibrin level was calculated as the difference between the concentration of D-dimers in the treated plasma and that present in the untreated plasma.

When the Level of D-dimers in the plasma was more than 4000 ng/ml, the sample was diluted after the degradation step.

The soluble fibrin used as the positive control was obtained by incubation of normal plasma with small doses of thrombin for a short period at the end of which the thrombin was blocked with heparin.

The plasma from the sample to be tested, and also the positive control and the negative control to assay the soluble fibrin, were assayed in the manner shown in Table III.

TABLE III

|  | Base D-dimers | SDF + base D-dimers |
| --- | --- | --- |
| Plasma | 200 µl | 200 µl |
| Pure AC | 20 µl | 20 µl |
| Tpa | — | 20 µl |
| Physiological serum | 40 µl | — |
|  | 15 min at +37° C. |  |
| Aprotinin | — | 20 µl |

Adding aprotinin blocked the plasmin at a predetermined time, leading to the degradation of fibrin alone and not of fibrinogen.

the positive and negative controls were reconstituted with ACd, i.e. AC diluted 1:5.

Preparation of AC:

| Citric acid, H$_2$O | MWt = 210.14 | 0.16 g |
| Trisodium citrate, 2 H$_2$O | MWt = 294.10 | 0.44 g |
| H$_2$O |  | 20 ml |

Results

Specificity of Measurements in normal healthy volunteers (n=180), the level of soluble fibrin was very small, 300 ng/ml or less.

Further, there was no correlation between the plasmatic concentration of soluble fibrin and that of D-dimers since after treating the patients with heparin, the concentration of fibrin dropped very rapidly while the concentration of D-dimers dropped much more slowly since it reflects degradation of the clot which persists after blocking coagulation activation.

Levels of D-Dimers and Soluble Fibrin Level in Patients Suspected of Thromboembolic Venous Disease or Pulmonary Embolism In Normal Healthy Volunteers (n=180):

The mean value was 80±106 ng/ml and of the 180 volunteers tested, 140 had an undetectable level of soluble degradable fibrin. The threshold value taken for a positive test was 300 ng/ml.

In Patients Suspected of Pulmonary Embolism or Deep Venous Thrombosis

Of the 38 patients with suspected pulmonary embolism, 23 were positive according to imaging analysis and of 49 with suspected deep venous thrombosis, 25 were positive, in accordance with the observation of abnormal compression of the proximal veins of the leg in ultrasound.

Of the two groups of patients, those presenting with pulmonary embolism (n=23) or a deep venous thrombosis (25), 2 had soluble fibrin counts which were false negatives, one of the group presenting with a pulmonary embolism (confirmed by angiography) and the other in the group of patients presenting with a deep venous thrombosis (conformed by ultrasound); however, these 2 patients had levels of D-dimers which were higher than the threshold value of 500 ng/ml. In contrast, the levels of D-dimers were normal (<500 ng/ml) in 2 patients (one of the group having a pulmonary embolism and the other in the group of patients presenting with deep venous thrombosis), while the levels of soluble degradable fibrin were >300 ng/ml. These levels of D-dimers which were false negatives were observed when the level of D-dimers was determined by the Lia Test® or by the Vidas® test.

With a combination of D-dimers and soluble fibrin, no false negatives were detected in the biological values.

The indices of pertinence (sensitivity, specificity, positive and negative predictive value) for the D-dimers, and the soluble degradable fibrin were calculated.

TABLE III

Sensitivity, specificity, positive and negative predictive value of D-dimers and soluble degradable fibrin

| | SDF+ | | D-dimers + soluble fibrin | |
|---|---|---|---|---|
| | EP | DVT | EP | DVT |
| PPV | 92% | 88% | 71% | 60% |
| NPV | 92% | 95% | 83% | 90% |
| Sensitivity | 96% | 96% | 96% | 96% |
| Sensitivity | 86% | 87% | 36% | 37% |

PPV = positive predictive value
NPV = negative predictive value
EP = pulmonary embolism
DVT = deep venous thrombosis
SDF = soluble degradable fibrin Change in Levels of D-Dimers and Soluble Degradable Fibrin in Patients Under Anti-Coagulation Treatment Rapid normalization of soluble degradable fibrin was observed in patients under non fractionated heparin or under low molecular weight heparin given in a curative dose. After day 1, the levels of soluble degradable fibrin were normal or at the upper limit of normal. Daily analysis of the levels showed that the soluble degradable fibrin remained within normal parameters during the treatment with heparin. In contrast, the levels of D-dimers reduced slowly and the levels did not reach normal levels during the treatment with heparin. In one patient, the soluble fibrin was further increased during therapeutic treatment, indicating an insufficient therapeutic effect.

Discussion

There exists a need for a non-invasive diagnostic tool suitable for diagnosing pulmonary embolism and/or deep venous thrombosis, which can allow an immediate decision to be made in the majority of cases as regards the treatment to be given.

This study was aimed at determining whether the combination of D-dimers and soluble degradable fibrin could be useful for the diagnosis of pulmonary embolism and/or deep venous thrombosis and to evaluate the efficiency of an anticoagulation treatment to inhibit thrombogenesis.

Concerning the sensitivity of measurements in pulmonary embolism and deep venous thrombosis: The 2 patients presenting false negative results relating to the level of D-dimers (one from the group with pulmonary embolism and the other from the group of patients presenting with deep venous thrombosis) had soluble degradable fibrin levels which were higher than the upper limit of the threshold value. This could have been due to an abnormal fibrin clot structure (congenital or acquired) rendering the clots abnormally resistant to fibrinolysis. This anomaly could contribute directly to an increased risk of thrombosis due to defective thrombolysis.

This hypofibrinolysis may explain the 3% to 5% of cases of "false negatives" for D-dimers in patients presenting a constituted thrombosis. In determining the soluble degradable fibrin, the fibrin is readily accessible to fibrinolytic enzymes. In contrast, the fibrin of the thrombus, when formed from fine and very tight fibrins, is less accessible to fibrinolytic enzymes, explaining the 3% to 5% of false negatives of D-dimers observed in thromboses. The negative levels relative to soluble degradable fibrin were detected in 2 patients (one from the group presenting with pulmonary embolism and the other in the group of patients presenting with a deep venous thrombosis) while the level of D-dimers in these 2 patients was more than 500 ng/ml. This could suggest that the thrombogenicity is a non evolutive process since the activity of the thrombin is transitory.

The inventors have demonstrated that a combination of the two tests (soluble degradable fibrin and D-dimers) may be used to distinguish a diagnosis of pulmonary embolism from deep venous thrombosis in patients.

In the majority of cases, plasmatic D-dimers satisfy the criteria required for a diagnosis of pulmonary embolism and deep venous thrombosis as they are sensitive markers for thrombosis but lack specificity (26-35).

It is now well established that D-dimers cannot be used to carry out a positive diagnosis of thromboembolic venous diseases as the test is not sufficiently specific. However, when the level of D-dimers is normal, the diagnosis of thromboembolic disease can be made in 95% of patients.

In this study, it has been shown that the specificity of soluble fibrin is much higher than that of D-dimers. This low specificity for measurements of D-dimers in diagnosing thromboembolic venous diseases may be due to degradation by local fibrinolytic enzymes of the fibrin present in the tissues. The products of soluble fibrin degradation formed locally in the tissues diffuse into the blood because of their relatively low molecular weight. This is supported by the observation that the level of D-dimers is often high in patients with inflammatory diseases.

In this study, it has also been shown that the level of soluble degradable fibrin is increased in thrombotic events; however, as soon as anti-coagulation treatments are administered, the concentration of soluble degradable fibrin decreases to a normal value over a few hours. This suggests that anti-coagulating drugs are capable of effectively blocking the thrombotic process. The persistence of the raised level of D-dimers is due to degradation of the thrombus formed before the anti-coagulation treatment. As a result, we propose that determining the soluble degradable fibrin to follow the effectiveness of anti-coagulant treatment or to test the effectiveness of novel anti-thrombotic drugs is of importance.

In conclusion, the results of this study suggest that determining soluble degradable fibrin in association with that of D-dimers may be considered to be a useful clinical tool for the diagnosis of deep venous thrombosis and pulmonary embolism and also of other thrombotic events. Further, it is suggested that soluble degradable fibrin may be useful in monitoring the effects of an anti-coagulation treatment.

REFERENCES

1. Arkel Y S, Ku D H, Le P, Carr A M. Comparison of a test for soluble fibrin polymer (TpP) with a standard quantitative ELISA for D-dimer in patients, without current thrombosis, who have cancer or renal disease. Thromb Haemost. 2001; 86: 1127-8.
2. Arkel Y S, Paidas M J, Ku D H. The use of coagulation activation markers (soluble fibrin polymer, TpP, prothrombin fragment 1.2, thrombin-antithrombin, and D-dimer) in the assessment of hypercoagulability in patients with inherited and acquired prothrombotic disorders. Blood Coagul Fibrinolysis. 2002; 13 :199-205.
3. Brimble K S, Ginsberg J S. Evaluation of the combination of a bedside D-dimer assay and enzyme-linked immunosorbent soluble fibrin assay in patients with suspected venous thromboembolism. Thromb Res. 1997; 88:291-7.
4. Dempfle C E, Dollman M, Lill H, Puzzovio D, Dessauer A, Heene D L. Binding of a new monoclonal antibody against N-terminal heptapeptide of fibrin alpha-chain to fibrin polymerization site 'A': effects of fibrinogen and fibrinogen derivatives, and pre-treatment of samples with NaSCN. Fibrinolysis. 1993; 4:79-86.
5. Dempfle C E, Pfitzner S A, Dollman M, Huck K, Stehle G, Heene D L. Comparison of immunological and functional assays for measurement of soluble fibrin. Thromb Haemost. 1995; 74:673-9.
6. Dempfle C E, Zips S, Ergul H, Heene D L; FACT study group. The fibrin assay comparison trial (FACT): correlation of soluble fibrin assays with D-dimer. Thromb Haemost. 2001; 86:1204-9.
7. Dempfle C E, Wurst M, Smolinski M, Lorenz S, Osika A, Olenik D, Fiedler F, Borggrefe M. Use of soluble fibrin antigen instead of D-dimer as fibrin-related marker may enhance the prognostic power of the ISTH overt DIC score. Thromb Haemost. 2004; 91:812-8.
8. Derhaschnig U, Laggner A N, Roggla M, Hirschi M M, Kapiotis S, Marsik C, Jilma B. Evaluation of coagulation markers for early diagnosis of acute coronary syndromes in the emergency room. Clin Chem. 2002; 48:1924-30.
9. Ginsberg J S, Siragusa S, Douketis J, Johnston M, Moffat K, Stevens P, Brill-Edwards P, Panju A, Patel A. Evaluation of a soluble fibrin assay in patients with suspected deep venous thrombosis. Thromb Haemost. 1995; 74:833-6.
10. Ginsberg J S, Siragusa S, Douketis J, Johnston M, Moffat K, Donovan D, McGinnis J, Brill-Edwards P, Panju A, Patel A, Weitz J I. Evaluation of a soluble fibrin assay in patients with suspected pulmonary embolism. Thromb Haemost. 1996; 75:551-4.
11. Hetland O, Knudsen A, Dickstein K, Nilsen D. W. Characteristics and prognostic impact of plasma fibrin monomer (soluble fibrin) in patients with coronary artery disease. Blood Coagul Fibrinolysis. 2002; 13:301-8.
12. Koga S. A novel molecular marker for thrombus formation and life prognosis—clinical usefulness of measurement of soluble fibrin monomer-fibrinogen complex (SF) Rinsho Byori. 2004; 52:355-61.
13. LaCapra S, Arkel Y S, Ku D H, Gibson D, Lake C, Lam X. The use of thrombus precursor protein, D-dimer, prothrombin fragment 1.2, and thrombin antithrombin in the exclusion of proximal deep venous thrombosis and pulmonary embolism. Blood Coagul Fibrinolysis. 2000; 11:371-7.
14. Mac Gillavry M R, Sanson B J, de Monye W, Lijmer J G, Huisman M V, Buller H R, Nieuwenhuizen W, Brandjes D P. Use of a new monoclonal antibody-based enzyme immunoassay for soluble fibrin to exclude pulmonary embolism. ANTELOPE-Study Group. Thromb Haemost. 2000; 84:474-7.
15. Nakahara K, Kazahaya Y, Shintani Y, Yamazumi K, Eguchi Y, Koga S, Wada H, Matsuda M. Measurement of soluble fibrin monomer-fibrinogen complex in plasmas derived from patients with various underlying clinical situations. Thromb Haemost. 2003; 89:832-6.
16. Nieuwenhuizen W, Hoegee-De Nobel E, Laterveer R. A rapid monoclonal antibody-based enzyme immunoassay (EIA) for the quantitative determination of soluble fibrin in plasma. Thromb Haemost. 1992; 68:273-7.
17. Nieuwenhuizen W. Soluble fibrin as a molecular marker for a pre-thrombotic state: a mini-review. Blood Coagul Fibrinolysis. 1993; 4:93-6.
18. Okajima K, Uchiba M, Murakami K, Okabe H, Takatsuki K. Determination of plasma soluble fibrin using a new ELISA method in patients with disseminated intravascular coagulation. Am J Hematol. 1996; 51:186-91.
19. Reber G, Bounameaux H, Perrier A, de Moerloose P. Performances of the fibrin monomer test for the exclusion of pulmonary embolism in symptomatic outpatients. Thromb Haemost. 1999; 81:221-3.
20. Scarano L, Prandoni P, Gavasso S, Gomiero W, Carraro G, Girolami A. Blood Coagul Failure of soluble fibrin polymers in the diagnosis of clinically suspected deep venous thrombosis. Fibrinolysis. 1999; 10:245-50.
21. Wada H, Sase T, Matsumoto T, Kushiya F, Sakakura M, Mori Y, Nishikawa M, Ohnishi K, Nakatani K, Gabazza E C, Shiku H, Nobori T. Increased soluble fibrin in plasma of patients with disseminated intravascular coagulation. Clin Appl Thromb Hemost. 2003; 9:233-40.
22. Brummel K E, Butenas S, and Mann K G. FXIII activation associated with a primary cleavage in the A-subunit at Arg-37 releasing an $NH_2$-terminal activation peptide (54), is coincident with FPA release. J Biol Chem, 1999; 274: 22862-22870
23. Nossel H L, Yudelman I, Canfield R E, Butler V P Jr, Spanondis K, Wilner G D, Qureshi G D. Measurement of fibrinopeptide A in human blood. J Clin Invest. 1974; 54:43-53
24. Shifman M A, Pizzo S V. The in vivo metabolism of antithrombin III and antithrombin III complexes. J Biol Chem. 1982; 257 :3243-8.
25. Lee L. V., Ewald G. A., McKenzie C. R, Eisenberg P. R. The Relationship of Soluble Fibrin and Cross-linked Fibrin Degradation Products to the Clinical Course of Myocardial Infarction. Arteriosclerosis, Thrombosis, and Vascular Biology. 1997, 17: 628-633.

26. Bounameaux H, Schneider P A, Siosman D, De Moerloose P, Reber G. Value of the plasma measurement of D-dimers in the diagnosis of venous thromboembolism. J Mal Vasco 1991; 16:133-6.
27. Kelly J, Rudd A, Lewis R R, Hunt B J. Plasma D-dimers in the diagnosis of venous thromboembolism. Arch Intern Med. 2002; 162:747-56.
28. Kevorkian J P, Halimi C, Segrestaa J M, Drouet L, Soria C. Monitoring of patients with deep-vein thrombosis during and after anticoagulation with D-dimer. Lancet. 1998; 351 :571-2.
29. Kuruvilla J, Wells P S, Morrow B, MacKinnon K, Keeney M, Kovacs M J. Prospective assessment of the natural history of positive D-dimer results in persons with acute venous thromboembolism (DVT or PE). Thromb Haemost. 2003; 89:284-7.
30. Nunes J P. D-dimers in diagnosis of pulmonary embolism. Lancet. 2002 Aug. 10; 360(9331):489.
31. van Beek E J, Schenk B E, Michel B C, van den Ende B, Brandjes D P, van der Heide Y T, Bossuyt P M, Buller H R. The role of plasma D-dimers concentration in the exclusion of pulmonary embolism. Br J Haematol. 1996; 92:725-32. Erratum in: Br J Haematol 1996; 95:218.
32. Perrier A, Roy P M, Aujesky D, Chagnon I, Howarth N, Gourdier A L, Leftheriotis G, Barghouth G, Cornuz J, Hayoz D, Bounameaux H. Diagnosing pulmonary embolism in outpatients with clinical assessment, D-dimer measurement, venous ultrasound, and helical computed tomography: a multicenter management study. Am J Med. 2004; 116:291-9.
33. Reber G, Bounameaux H, Perrier A, de Moerloose P. Evaluation of advanced D-dimer assay for the exclusion of venous thromboembolism. Thromb Res. 2002; 107:197-200.
34. Wells P S, Anderson D R, Rodger M, Forgie M, Kearon C, Dreyer J, Kovacs G, Mitchell M, Lewandowski B, Kovacs M J. Evaluation of D-dimer in the diagnosis of suspected deep-vein thrombosis. N Engl J Med. 2003; 349:1227-35.
35. Wells P S, Anderson D R, Rodger M, Stielll, Dreyer J F, Barnes D, Forgie M, Kovacs G, Ward J, Kovacs M J. Excluding pulmonary embolism at the bedside without diagnostic imaging: management of patients with suspected pulmonary embolism presenting to the emergency department by using a simple clinical model and D-dimer. Ann Intern Med. 2001; 135:98-107.

The invention claimed is:

1. An in vitro method for diagnosing coagulation activation linked to a risk of thromboembolic disease starting from a blood sample removed from a patient, comprising:
   i) measuring a quantity of fibrin degradation products contained in the sample, by measuring a quantity of D-dimers present in the sample and constituting a base level of D-dimers;
   ii) treating the sample by incubation with a plasminogen activator with a high affinity for fibrin (Pa-Fb sp) under conditions allowing degradation of soluble fibrin contained in the sample into degradation products without resulting in degradation of fibrinogen, and measuring a quantity of D-dimers contained in the treated sample;
   iii) calculating a difference between the quantity of D-dimers measured after activation by the Pa-Fb sp activator in step ii) and the quantity of D-dimers before said activation measured in step i), said difference constituting a degree of degradation of soluble fibrin (SDF);
   iv) comparing the level of D-dimers measured in step i) with a normal threshold value determined for said degradation product and comparing the level of SDF calculated in step iii) with a normal threshold value determined for SDF;
   a risk of thromboembolic disease existing if at least one of the levels of D-dimers measured in step i) or the calculated level of SDF obtained in step iii) is higher than the respective determined normal value and said risk being excluded when the level of D-dimers obtained in step i) and the level of SDF obtained in step iii) are lower than the respective normal threshold values.

2. The method according to claim 1, for investigating a thromboembolic venous disease.

3. The method according to claim 1, applied to investigating venous thrombus formation.

4. The method according to claim 1, for the diagnosis of a deep venous thrombosis.

5. The method according to claim 1, for the diagnosis of a pulmonary embolism.

6. The method according to claim 1, wherein the blood sample is a plasma sample.

7. The method according to claim 1, wherein the blood sample is that of a patient benefiting from an anti-coagulation therapy.

8. The method according to claim 5, wherein the Pa-Fb sp plasminogen activator is t-PA.

9. The method according to claim 1, wherein fibrinogen degradation is prevented by adding a plasmin inhibitor.

10. The method according to claim 9, wherein the plasmin inhibitor is aprotinin, which is added after incubating the sample for 15 minutes at 37° C. with the Pa-Fb plasminogen activator.

11. The method according to claim 1, wherein prior to incubation of the sample with the Pa-Fb plasminogen activator, an anti-coagulant is added to the sample.

12. The method according to claim 1, further comprising assaying the degradation products of soluble fibrin in a negative control sample and in a positive control sample.

13. The method according to claim 1, wherein the D-dimers are measured using anti-D-dimer monoclonal antibody.

14. The method according to claim 1, further comprising measuring the SDF present in a positive control sample constituted by a normal plasma sample by carrying out steps comprising:
   i) incubating a plasma sample with a coagulation activator to allow the formation of soluble fibrin without forming a fibrin clot;
   ii) incubating the treated sample with a coagulation inhibitor in a quantity sufficient to block coagulation,
   iii) bringing the prepared sample comprising soluble fibrin monomers into contact with a plasminogen activator with a high affinity for fibrin (Pa-Fb sp) under conditions allowing degradation of the soluble fibrin contained in the sample into its degradation products, especially D-dimers, without degrading the fibrinogen.

15. The method according to claim 1, wherein the normal threshold value for the quantity of D-dimers is 500 ng/ml and the normal threshold value for SDF is 300 ng/ml, a diagnosis excluding thromboembolic disease being made when the measured values of the test sample are less than the two respective threshold values.

16. A kit for diagnosing thromboembolic disease using a method according to claim 1, comprising:
   anti D-dimer monoclonal antibodies;
   a plasminogen activator with a high specificity for fibrin (Pa-Fb sp);
   a plasmin inhibitor; and a positive control sample for soluble fibrin and if appropriate a negative control sample.

17. The method according to claim 14, wherein the coagulation activator is a small quantity of thrombin to induce the formation of soluble fibrin.

18. The method according to claim 14, wherein the plasminogen activator with a high affinity for fibrin (Pa-Fb sp) is t-PA.

19. The method of according to claim 11, wherein the anti-coagulant comprises citric acid and trisodium citrate.

20. The method of according to claim 14, wherein the coagulation inhibitor is heparin or hirudin.

* * * * *